(12) United States Patent  
Lundstrom et al.

(10) Patent No.: US 8,899,095 B2
(45) Date of Patent: Dec. 2, 2014

(54) MRI COMPATIBLE AND AIR-ACTUATED OLFACTOMETER

(75) Inventors: Johan Nils Lundstrom, Philadelphia, PA (US); Amy Russell Gordon, New York, NY (US)

(73) Assignee: Monell Chemical Senses Center, Philadelphia, PA (US)

( * ) Notice: Subject to any disclaimer, the term of this patent is extended or adjusted under 35 U.S.C. 154(b) by 451 days.

(21) Appl. No.: 13/497,066

(22) PCT Filed: Sep. 21, 2010

(86) PCT No.: PCT/US2010/049605
§ 371 (c)(1),
(2), (4) Date: Apr. 3, 2012

(87) PCT Pub. No.: WO2011/035284
PCT Pub. Date: Mar. 24, 2011

(65) Prior Publication Data
US 2012/0184828 A1     Jul. 19, 2012

Related U.S. Application Data

(60) Provisional application No. 61/244,171, filed on Sep. 21, 2009.

(51) Int. Cl.
*G01N 33/497*   (2006.01)
*A61B 5/055*    (2006.01)
*A61B 5/00*     (2006.01)

(52) U.S. Cl.
CPC ............. *A61B 5/055* (2013.01); *G01N 33/497* (2013.01); *A61B 5/4011* (2013.01)
USPC ........................................ 73/23.3

(58) Field of Classification Search
CPC ........................... A61B 5/4011; G01N 33/497
USPC ............................................ 73/23.3; 600/303
See application file for complete search history.

(56) References Cited

U.S. PATENT DOCUMENTS

| 4,388,272 | A | | 6/1983 | Gesteland |
| 5,727,186 | A | * | 3/1998 | Shervington et al. ............. 703/6 |
| 5,762,268 | A | * | 6/1998 | Shervington et al. ........... 239/70 |
| 6,325,475 | B1 | | 12/2001 | Hayes et al. |
| 6,772,762 | B2 | * | 8/2004 | Piesinger ...................... 128/847 |
| 7,377,493 | B2 | * | 5/2008 | Thomas ......................... 261/30 |
| 8,557,116 | B2 | * | 10/2013 | Johnson et al. ............ 210/323.2 |
| 2001/0041366 | A1 | | 11/2001 | Lewis et al. |
| 2002/0139170 | A1 | | 10/2002 | Doty |
| 2007/0138660 | A1 | * | 6/2007 | Guo ............................... 261/26 |

FOREIGN PATENT DOCUMENTS

WO  WO 2011/035284   3/2011

* cited by examiner

*Primary Examiner* — Hezron E Williams
*Assistant Examiner* — Rodney T Frank
(74) *Attorney, Agent, or Firm* — Baker & Hostetler LLP

(57) ABSTRACT

An olfactometer is disclosed. Such an olfactometer may include a control unit, an odor box, and a nose piece in communication with the odor box. The control unit may include a reservoir, and a compressor for supplying pressurized air to the reservoir. The odor box may include at least one compressed air actuated valve, and at least one odor canister in communication with the valve. A compressed air flow and a breathable air flow are both released from the reservoir and directed to the valve. The compressed air flow actuates the valve to thereby direct the breathable air to the odor canister to odorize the breathable air. The odorized breathable air is then directed to the nose piece.

23 Claims, 4 Drawing Sheets

MRI COMPATIBLE AND AIR-ACTUATED OLFACTOMETER

CROSS-REFERENCE TO RELATED APPLICATIONS

This application is the National Stage of International Application No. PCT/US2010/049605 filed Sep. 21, 2010, which claims the benefit of U.S. Application No. 61/244,171, filed Sep. 21, 2009, the disclosures of which are incorporated herein by reference in their entireties.

TECHNICAL FIELD

The present invention generally relates to an odor delivery system. More particularly, the present invention relates to an odor delivery system for presenting precise amounts of odorants to a test subject.

BACKGROUND

The first imaging study investigating the neuronal processing of odors in humans was published in 1992 and although almost two decades has passed since this seminal study, our knowledge about the central processing of olfactory information remains limited. One factor contributing to this gap in knowledge is the major obstacle of delivering odor stimuli to subjects inside an MRI scanner.

Presenting controlled odorous stimuli to the MRI scanner in a manner suitable for scientific experimentation is difficult due to two overarching factors. First, the environment inside an MRI scanner is hostile to ferrous items, items coated with ferrous material, and any significant amount of metal, ferrous or not. The scanner itself is a powerful magnet (ranging in field strength from 1.5 to 7 Tesla) capable of attracting even minute amounts of ferrous material located within the scanner suite; the force with which these items would be pulled into the scanner bore poses a life-threatening risk for anyone lying inside. Moreover, larger quantities of denser metal in close vicinity to the scanner induce distortions in the acquired images that render them unusable. Therefore, all components placed inside the scanner room must be made entirely out of plastic, wood, and/or limited quantities of aluminum, brass, and/or high-grade stainless steel. Second, stable, controllable airflow and stimulus presentation are required for good measurement. Delivered stimuli preferably display several characteristics, such as a square-shaped form (low, steep rise-time; stable concentration; steep offset), a fast and consistent onset enabling synchronous delivery with other presented stimuli, and a presentation devoid of tactile cues (such as a change in airflow).

SUMMARY

The olfactometer described here resolves at least some of the issues listed above by utilizing MRI-compatible air-actuated valves, which control odorant delivery from within the MRI-suite, in close proximity to the MRI scanner bore and the subject inside.

In that regard, such an olfactometer may include a control unit, a non-magnetic odor box, and a nose piece in communication with the odor box. The control unit may include a reservoir, and a compressor configured to supply pressurized air to the reservoir. The odor box may include at least one compressed air actuated valve, and at least one odor canister in communication with the valve. The nose piece may be in communication with the odor box. A compressed air flow is released from the reservoir and directed to the valve to thereby actuate the valve. The actuated valve may direct a breathable air flow to the odor canister to thereby odorize the breathable air flow. The odorized breathable air flow may then be directed to the nose piece.

A method of determining an individual's olfactory central processing is also disclosed. Such a method may include placing an odor box in a room along with a magnetic resonance imaging (MRI) scanner machine. The odor box may have an odor canister containing an odor, and an air actuated valve that is configured to selectively direct a breathable air into the odor canister. The valve may be actuated using compressed air to thereby direct the breathable air into the odor canister. The odorized breathable air is then directed to a test subject that is inside the MRI scanner.

DETAILED DESCRIPTION OF ILLUSTRATIVE EMBODIMENTS

Figure 1:
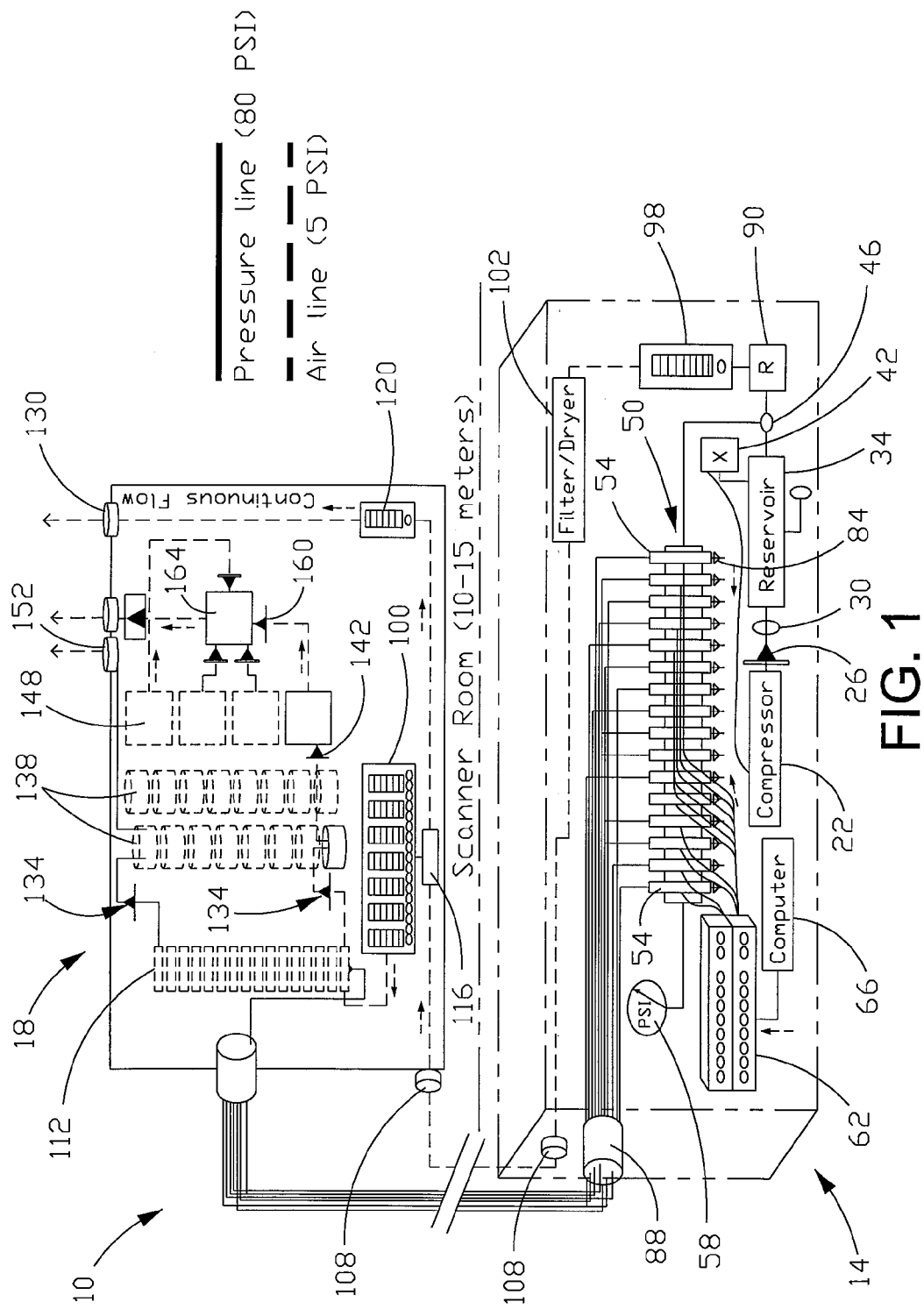
FIG. 1 is a schematic view showing a control unit and an odor box of an olfactometer in accordance with one embodiment.

FIG. 1 shows a schematic of an olfactometer 10 according to one embodiment. Olfactometer 10 may enable one to perform event related olfactory experiments in a functional magneticresonance imaging scanner (fMRI). Olfactometer 10 may take into account all important sensory—and odorant—related aspects of odor delivery. As shown olfactometer 10 includes a control unit 14 and an odor box 18.

As shown in FIG. 1, control unit 14 includes a compressor 22 that provides olfactometer 10 with compressed air to control air-actuated (pneumatic) valves located within odor box 18 and with breathable air that carries stimuli to the subject. Compressor 22 is connected to a high-pressure check valve 26, which is connected to a three-way direction switch 30. Directional switch 30 provides the option for either supplying the system with pressure from an external air-source or to use compressor 22. In the latter case, air is directed to an air reservoir 34. Check valve 26 is in place to prevent the compressed air from traveling backwards towards compressor 22. To allow either emergency pressure release of the entire system or just a convenient way of depressurizing reservoir 34, a two-way ball valve 38 is connected to air reservoir 34. Two additional connections exist on air reservoir 34: (a) a two-poled pressure switch 42 is mounted on reservoir 34 to regulate the compressor's high and low operating points, thus allowing the system to maintain a stable pressure in the range of about 70 to 80 PSI; and (b) a two-way splitter 46 is mounted on reservoir 34 to divide the out-flowing air into the separate compressed air and breathable air systems.

The air flow directed to the compressed air system enters through a manifold 50 of two-way solenoid valves 54. A pressure meter 58 mounted to manifold 50 informs the operator that the operating pressure within the system is above the required actuating pressure for the compressed air actuated pneumatics valves in odor box 18. Solenoid valves 54 are regulated by a valve control unit 62. Control unit 62 converts the digital TTL signals sent from computer 66 into 5V analog signals compatible with the valves. Additional benefits of using a valve control unit between computer 66 and solenoid valves 54 is that one does not need to use complicated DAQ boards and with that the laborious coding needed to control them is eliminated. The use of valve control units with a standard desktop computer allows a theoretical number of 80 solenoid valves 54, which leaves only space requirements and costs as limitations to the number of possible odor channels. Furthermore, use of the valve control unit allows the use of a standard, off-the-shelf stimulus presentation program as a stimulus trigger.

Figure 4:
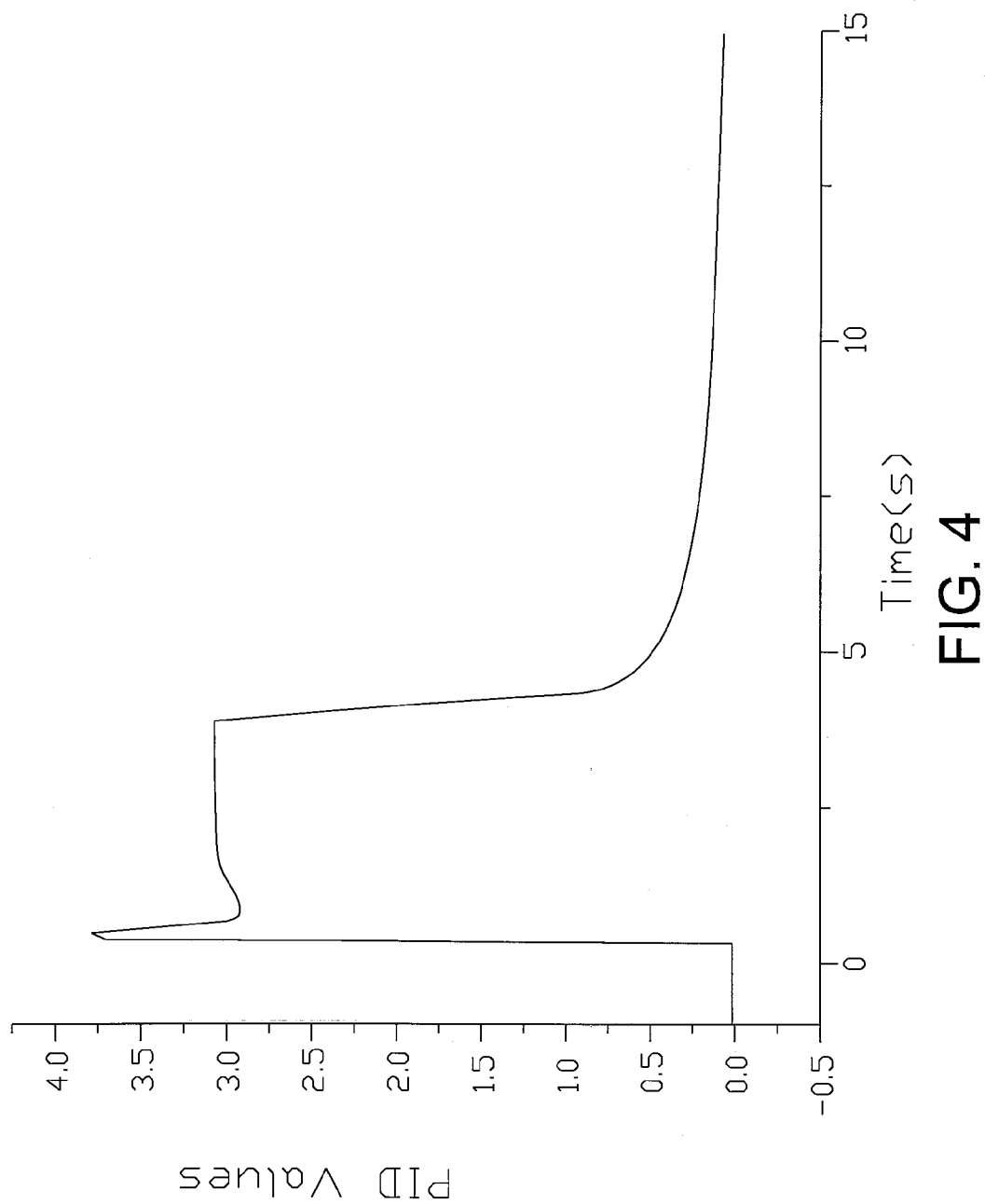
FIG. 4 is a table showing data recorded using a photoionization detector that depicts the fast onset and offset of the odor stimulus at the nose piece and also demonstrates the limited amount of residual odor contamination that is presented to the nose after odor offset.

In particular the stimulus presentation program on the computer 66 sends a TTL pulse to valve control unit 62, which then switches solenoid valve 54 from a closed position to an open position. This releases high pressure air through the compressed air line, which triggers the pneumatic valve located within odor box 18 inside the scanner room. To allow a fast de-pressurization of the line and fat closure of the pneumatic valve, a quick exhaust connection 84 is located on the exit port of each valve 54. A decrease in pressure on either side of the pneumatic valve will trigger quick exhaust connection 84 and the rapid de-pressurization of the compressed air line. This feature is one of the elements behind the fast offset times recorded with this system. FIG. 4 depicts recorded stimulus onset and offset times recorded with a photoionization detector for the olfactometer 10. From individual quick exhaust connection 84, the individual compressed air lines project from the solenoid valves 54 to a multiple connector socket 88 mounted in control unit 14, which allows for fast and line-matched linkage to complementary multiple connector socket 88 leading to odor box 18.

The flow directed to the breathable air system enters through a pressure regulator 90 which reduces the pressure of the compressed air emerging from air reservoir 34 (about 80 PSI) to a breathable pressure. This low pressure air is channeled through a needle valve-regulated flowmeter 98, which allows the experimenter to set the flow of breathable air sent to odor box 18 equal to the total necessary for outtakes from all the individual odor lines and the continuous flow line. This feature assures that there is not a buildup of pressure over time in the system, which would disrupt the calibration of flowmeters 100 downstream. The breathable air should be as odorless as possible; this prevents unanticipated odor mixing effects and contamination of the supposedly odor-free baseline recordings. The breathable air is dehumidified and filtered as it passes through a dual-purpose dehumidification and purification module 102. The dry, clean breathable air is subsequently channeled through a quick disconnect coupling 108 leading to odor box 18, which is adjacent to multiple connector 88 used for the compressed air system.

Odor box 18 is built out of aluminum frames with Plexiglas side walls. This allows odor box 18 to be light, easy to transport, easy to modify due to the flexible material, non-magnetic, and easy to work inside due to the good visibility created by the Plexiglas sides. By being non-magnetic, odor box 18 may be in the same room as the MRI machine while it is in use. The compressed air and breathable air, within their respective tubing, are transported into the scanner room to odor box 18 in a protective bundle to ensure strain relief for the tubing. At each end of the tubing bundle are multiple connector and quick-disconnect plugs for the compressed air and breathable air respectively. At odor box 18, the compressed air and breathable air plug into mounted multiple connectors 88 and quick-disconnect couplings 108, as described for control unit 14.

Figure 2:
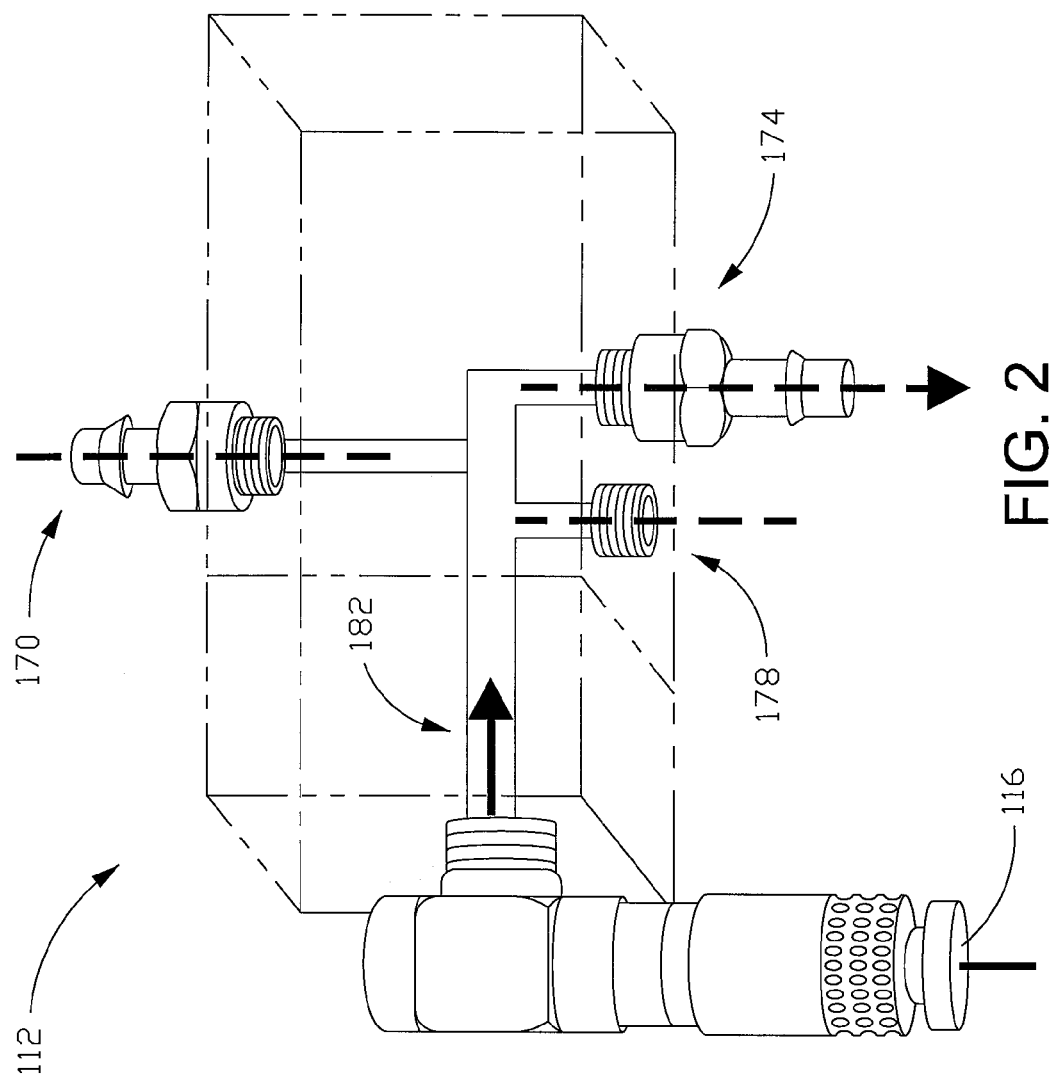
FIG. 2 is a schematic view of a four-way, compressed air-actuated valve located within the odor box described in FIG. 1, in accordance with one embodiment.

The incoming compressed air lines are connected to their respective pneumatic valves 112, as depicted in FIGS. 1 and 2. As shown, the line connect to quick exhaust connections 116 with a function similar to that previously described for quick exhaust connection 84 previously described.

The incoming breathable air line is directed from the quick disconnect coupling 108 mounted on the side of odor box 18 to a PTFE breathable manifold 116. Manifold 116 serves to evenly divide the airflow into odor line-specific needle-regulated flowmeters 100. In addition, the flow is diverted to a flowmeter 120 regulating the air used for the single continuous flow line. The typical olfactometer design features odor lines that are separated and switched at the control unit located outside the scanner suite, which allows for the use of solenoid valves to shift the active odor channel. However, that design also renders it difficult to deliver a stimulus with square-shaped characteristics, such as the steep onset and offset. Moreover, that design suffers from greater contamination problems since the lines are infused with odor earlier (outside the scanner suite). The design for olfactometer 10 features a single, communal odor-free breathable air line entering odor box 18 in the scanner suite, thereby foregoing intruding odors within the breathable air system until the very end. As a result, the amount of contaminated tubing that needs to be replaced following each experiment is kept to a minimum, thereby lowering cost of experimentation. The use of individual flowmeters for each odor line allows the use of separate flows during the experiment without dependence on expensive mass-flow control units, which require more expensive advanced control software to operate. The continuous flow prevents any tactile sensation of the switches that occur between stimulus conditions. This particular feature is described in detail below in reference to FIG. 3. The continuous flow exits odor box 18 via a quick disconnect coupling 130 leading to the nose piece. From the flowmeters, the odor lines are directed to the compressed air pneumatic valves 112.

After pneumatic valves 112, the air stream passes a check valve 134 before entering an odor canister 138. Each odor canister 138 may be a glass wash-bottle, which may help achieve accurate presentation of liquid odor sources with a limited risk of contamination. Many odor sources will break down plastic canisters, the alternative for use inside the scanner suite. In addition, the design may allow for flexibility of odor sources, which can be liquid or solid, in scenarios where real odor sources are sought (e.g. an actual apple for an apple odor). After passing through the odor canister, the breathable air passes yet another check valve 142 before entering an initial PTFE odor mixing manifold 148. The exceptions are the breathable air flowing through the continuous flow line and the breathable air flowing through the odor line designated as control, which contains no odor source; to avoid contamination, this line proceeds directly from odor canisters 138 to a quick disconnect coupling 152 and onward to the nose piece described in FIG. 3. The use of check valves both immediately before and after odor canisters 138 maintains the pressure within the canister, ensuring that the next odor pulse does not have to repressurize the canister. As air pressure within the canister remains steady, the arrival of new incoming breathable air immediately pushes an equal volume of already-odorized breathable air forward, past the check valve. This additional feature may lower the stimulus onset time dramatically. Moreover, the use of check valves immediately before odor canister 138 serves to prevent back contamination of the incoming odor free breathable air lines. Each initial PTFE odor mixing manifold 148 receives input from up to four breathable air lines, and the outputs are integrated in a secondary PTFE odor mixing manifold 164 further downstream. By limiting the inner size of these mixing manifolds 148 and using a multi-step mixing process, the dead space in each manifold that must be filled before odorized air flows forward is also kept to a minimum.

Before entering the secondary PTFE odor mixing manifold, all lines pass an additional check valve 160. From the final PTFE odor mixing manifold 148, the odorized breathable air is sent to a pressure release valve 164, which is in place as a safety measure. Preferably, pressure from the compressed air line is not able to enter the breathable air line due to the triple protection of high pressure regulator 90 and the two separate flow meters 98 and 100. However, in the event of a catastrophic failure of valve controller 62, it is possible that all individual odor channels opens up simultaneously, to thereby create a very high flow to the subject. In the event of such a sharp rise in pressure, the pressure release valve will prevent more than 5 liters per minute from reaching the subject; any excess flow is vented into the scanner room. From the pressure release valve, the odor line continues to the nose piece.

FIG. 2 is a detailed view of a four way pneumatic valve 112 having four ports 170, 174, 178, and 182. When not activated, breathable air enters in port 170 and flows out port 178, which releases the breathable air into odor box 18. When compressed air is delivered to pilot port 182, the valve shifts the outflow to port 174, which releases the breathable air to the downstream odor canisters 138 shown in FIG. 1. The high pressure in individual channel, together with small inner dimension of the tubing used for the compressed air channels, allows for a very fast stimulus onset and offset. Stimulus offset is further accelerated by the use of a quick exhaust connection at pilot port 116. Alternatively, the exhausted odor-free breathable air emitted from port 178 can be captured and removed from odor box 18. The flow pattern described above is designed to rinse the odor box of potential residual odors thereby avoiding the buildup of odor contamination during scanning. The amount of air flowing into odor box 18, in combination of the low risk of possible contaminations, also prevents residual odors evacuated from odor box 18 to reach suprathreshold levels.

Figure 3:
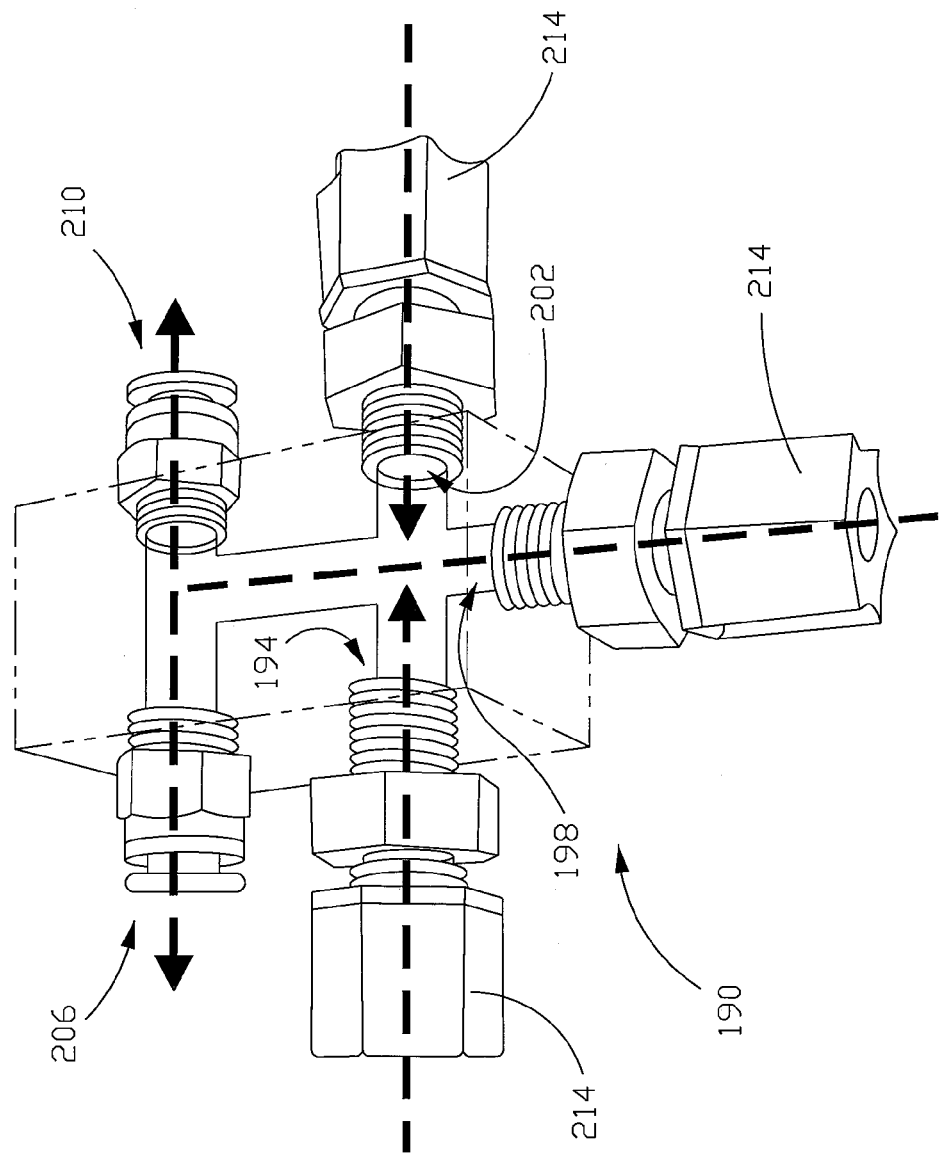
FIG. 3 is a schematic view of a nose piece designed to merge air lines inside the scanner bore of an MRI machine in accordance with one embodiment.

FIG. 3 depicts a nose piece 190 for the test subject. As shown, nose piece 190 has five ports 194, 198, 202, 206, and 210. The three ports (194, 198, and 202) that receive inputs from odor box 18 are fitted with a check valve 214 to prevent backflow of breathable air and to maintain pressure in each respective line. Port 194 receives the odor line carrying the odorant that is about to be presented. Port 202 receives the odor line carrying non-odorized control air. Port 198 receives the continuous flow line that is used to conceal the tactile sensations—the "puffs"—caused by the rapid switching between stimulus conditions, between the odor port 194 and control port 202 before and after an odor presentation. PTFE nose piece 190 serves as the final mixing manifold, inside which the breathable air delivered through ports 194 or 202 is embedded into the low continuous flow, and the sudden drops and rises in pressure created by switching are defused. A steady flow of odorized breathable air exits nose piece 190 via ports 206 and 210. The use of two separate exit ports assures that an equal amount of exiting breathable air enters each nostril. Lines emerging from ports 206 and 210 can transport breathable air to the nostrils via anatomically-shaped PTFE pieces that rest inside the nostrils or via a mask for simultaneous bi-nostril presentation.

The foregoing description is provided for the purpose of explanation and is not to be construed as limiting the invention. While the invention has been described with reference to preferred embodiments or preferred methods, it is understood that the words which have been used herein are words of description and illustration, rather than words of limitation. Furthermore, although the invention has been described herein with reference to particular structure, methods, and embodiments, the invention is not intended to be limited to the particulars disclosed herein, as the invention extends to all structures, methods and uses that are within the scope of the appended claims. Further, several advantages have been described that flow from the structure and methods; the present invention is not limited to structure and methods that encompass any or all of these advantages. Those skilled in olfactory technology, having the benefit of the teachings of this specification, may effect numerous modifications to the invention as described herein, and changes can be made without departing from the scope and spirit of the invention as defined by the appended claims. Furthermore, any features of one described embodiment can be applicable to the other embodiments described herein. For example, any features or advantages related to the design of the control unit, valves and odor box with respect to discussion of a particular olfactometer embodiment can be applicable to any other olfactometer embodiments. Additionally, while the embodiment illustrated includes a single odor line extending from the odor box to the nose piece, it should be understood that multiple odor lines may extend from the odor box to the nose piece. In such a case the nose piece would act as the mixing manifold.

What is claimed:

1. An olfactometer comprising:
a control unit including a reservoir, and a compressor configured to supply pressurized air to the reservoir;
a non-magnetic odor box including at least one compressed air actuated valve, and at least one odor canister in communication with the valve; and
a nose piece in communication with the odor box,
wherein (i) a compressed air flow is released from the reservoir and directed to the valve, to thereby actuate the valve, (ii) the actuated valve directs a breathable air flow to the odor canister to thereby odorize the breathable air flow, and (iii) the odorized breathable air flow is directed to the nose piece.

2. The olfactometer of claim 1, wherein the odor box includes a plurality of odor canisters.

3. The olfactometer of claim 1, wherein the odor box includes a check valve before and after the odor canister.

4. The olfactometer of claim 1, wherein the air actuated valve is a pneumatic valve.

5. The olfactometer of claim 4, wherein the pneumatic valve includes four ports.

6. The olfactometer of claim 5, wherein (i) the breathable air flow enters a first port and flows out a second port when the valve is not activated, and (ii) the breathable air flow flows out a third port that directs the breathable air to the odor canister, when the valve is activated.

7. The olfactometer of claim 1, wherein the odor box includes a mixing manifold, and the breathable air enters the mixing manifold after leaving the odor canister.

8. The olfactometer of claim 1, wherein the nose piece includes a first port that is configured to receive the odorized breathable air flow from the odor canister, and an exit port that is configured to direct the ordorized breathable air flow to a nose.

9. The olfactometer of claim 8, wherein the nose piece further includes a second port that is configured to receive a non-odorized breathable air flow.

10. The olfactometer of claim 9, wherein the nose piece further includes a third port that is configured to receive a continuous flow of breathable air.

11. The olfactometer of claim 1, wherein both the compressed air flow and the breathable air flow are released from the reservoir.

12. The olfactometer of claim 1, wherein the control unit includes a solenoid valve that is configured to release the compressed air flow from the reservoir to the valve.

13. The olfactometer of claim 1, wherein the odor box includes walls made of a transparent non-magnetic material.

14. An olfactometer comprising:
   a control unit having a compressor that is configured to supply a compressed air flow; and
   a non-magnetic odor box including at least one compressed air actuated valve, and at least one odor canister in communication with the valve, the valve being configured to direct breathable air to the odor canister upon actuation of the valve by the compressed air flow.

15. The olfactometer of claim 14, wherein the control unit includes a reservoir, and the compressor is configured to supply pressurized air to the reservoir.

16. The olfactometer of claim 14, further comprising a nose piece that is in communication with the odor box.

17. The olfactometer of claim 14, wherein the compressed air flow is released from the reservoir and directed to the valve.

18. The olfactometer of claim 14, wherein the odor box includes a plurality of odor canisters.

19. The olfactometer of claim 14, wherein the odor box includes a check valve before and after the odor canister.

20. The olfactometer of claim 14, wherein the odor box includes a mixing manifold, and the breathable air enters the mixing manifold after leaving the odor canister.

21. A method of determining an individual's olfactory central processing, the method comprising:
   placing an odor box in a room along with a magnetic resonance imaging (MRI) scanner machine, the odor box having an odor canister containing an odor, and an air actuated valve that is configured to selectively direct a breathable air into the odor canister;
   actuating the valve using compressed air to thereby direct the breathable air into the odor canister; and
   delivering the odorized breathable air to a test subject that is inside the MRI scanner.

22. The method of claim 21, wherein the compressed air and the breathable air released from a reservoir.

23. The method of claim 21, wherein the odor box is made from a non-magnetic material.

* * * * *